United States Patent [19]

Inue

[11] Patent Number: 5,393,793
[45] Date of Patent: Feb. 28, 1995

[54] OXIDE-BASED CATALYST, PRODUCTION THEREOF, AND CATALYTIC HYDROGENATION OF $CO_2$ USING SAID CATALYST

[76] Inventor: Tomoyuki Inui, 5-43, Hatoyama 1-chome, Uji-shi, Kyoto 611, Japan

[21] Appl. No.: 39,229

[22] PCT Filed: Aug. 17, 1992

[86] PCT No.: PCT/JP92/01039
§ 371 Date: Apr. 19, 1993
§ 102(e) Date: Apr. 19, 1993

[87] PCT Pub. No.: WO93/03837
PCT Pub. Date: Mar. 4, 1993

[30] Foreign Application Priority Data

Aug. 21, 1991 [JP] Japan .................. 3-235439

[51] Int. Cl.$^6$ .......................... C07C 27/06; B01J 23/10
[52] U.S. Cl. ........................ 518/713; 518/714; 502/302; 502/303
[58] Field of Search .............. 502/302, 303; 518/713, 518/714

[56] References Cited

U.S. PATENT DOCUMENTS 3,929,670 12/1975 Kudo et al. ............... 252/455 R
4,789,502 12/1988 Slaugh ........................ 260/413

FOREIGN PATENT DOCUMENTS 58-92460 6/1973 Japan .
4-120191 4/1992 Japan .
2109263 6/1983 United Kingdom .

*Primary Examiner*—Asok Pal
*Assistant Examiner*—P. Achutamurthy
*Attorney, Agent, or Firm*—Armstrong, Westerman, Hattori, McLeland & Naughton

[57] ABSTRACT

A compound oxide $X_1$ having the oxide composition $CuO$-$ZnO$-$Cr_2O_3$-$Al_2O_3$ is physically admixed with a compound oxide $X_2$ prepared by impregnating $\gamma$-$Al_2O_3$ with $La(NO_3)_3$ and firing the same, to give a $CuO$-$ZnO$-$Cr_2O_3$-$Al_2O_3$-$La_2O_3$-based compound oxide with an $La_2O_3$ addition level of 4% by weight. This compound oxide is reduced and packed into a reactor and a mixed gas composed of $CO_2$ and $H_2$ in a mole ratio of 1:3 is fed to the reactor, whereby methanol is obtained in high yield. The total conversion of $CO_2$ amounts to 31.0%, the conversion to methanol being 22.9% (selectivity toward methanol 73.9%). When the pressure is 80 atmospheres, the conversion of $CO_2$ amounts to 39%, the conversion to methanol being 29%.

9 Claims, 2 Drawing Sheets

OXIDE-BASED CATALYST, PRODUCTION THEREOF, AND CATALYTIC HYDROGENATION OF CO₂ USING SAID CATALYST

TECHNICAL FIELD

The present invention relates to an oxide-based catalyst comprising a compound oxide and a method of producing the same. The invention also relates to a method of catalytically hydrogenating $CO_2$ using said catalyst.

BACKGROUND ART

Prior Art

In recent years, global warming due to accumulation of $CO_2$ has become one of the serious environmental problems. It is an urgent necessity to reduce the amount of $CO_2$ emitted or discharged. If carbon dioxide can be converted to a useful substance, for example methanol or a liquid fuel, for reuse as a resource, it will become possible to solve the global warming problem and at the same time achieve a saving of petroleum resources.

Various proposals have already been made for the production of methanol by catalytic hydrogenation of $CO_2$ and studies on methanol synthesis catalysts therefor are in progress. Catalysts known for that purpose include oxide-based catalysts, metal catalysts and alloy catalysts. Among these, oxide-based catalysts are known to show good performance characteristics. The following oxide-based catalysts may be mentioned as typical examples: ZnO, $ZrO_2$, Cu/ZnO, Cu/oxide, $Cr_2O_3$/ZnO, Cu/ZnO/oxide, Cu/ZnO/$Al_2O_3$, ZnO/oxide, Cu/ZnO/$Cr_2O_3$/$Al_2O_3$, etc.

A method is also known which comprises synthesizing a methanol-rich gas by catalytic hydrogenation of $CO_2$ and at the same time synthesizing liquid hydrocarbons directly from the gaseous reaction mixture.

Thus, papers presented by the present inventors, namely Abstracts of papers for the 1984 Spring Meeting of the Chemical Society of Japan, vol. I, page 308, Abstracts of Papers for the 33rd Annual Meeting of the Japan Petroleum Institute, Special Lectures, and the 34th Meeting for Reading Research Papers, pages 71–74 and Preprints for the 66th Catalysis Forum (A) held by the Catalysis Society of Japan, page 118, disclose a process in which a first reactor and a second reactor are connected in series and in which, in the first reactor, a methanol-rich gas is produced from $CO_2$ and $H_2$ using a reduced CuO/ZnO/$Cr_2O_3$/$Al_2O_3$ catalyst or a catalyst derived therefrom by modification with Pd, Rh, Ru or Ag, the gas from the first reactor is fed, as such, to the second reactor and, in the second reactor, said gas is contacted with an H-form Fe-silicate catalyst for conversion thereof into a liquid hydrocarbon-rich fraction.

Currently, this process is one of the most attractive ones since it has the possibility of achieving, by a single effort, both the reduction of $CO_2$, which is regarded as the cause of global warming, and the saving of petroleum resources.

Problems Which the Invention is to Solve

If, in the above-mentioned serial process reported by the present inventors, namely in the step of producing methanol from $CO_2$ and $H_2$ using a reduced CuO/ZnO/$Cr_2O_3$/$Al_2O_3$ catalyst or a catalyst derived therefrom by modification with Pd, Rh, Ru or Ag, the conversion of $CO_2$ and the selectivity toward methanol can be further increased, the industrial or commercial significance of said process will reach the stage of perfection.

It is an object of the invention, which has been completed under such circumstances, to provide a novel oxide-based catalyst capable of giving a high $CO_2$ conversion and a high selectivity toward methanol in the catalytic hydrogenation of $CO_2$, a method of producing said catalyst and a commercially advantageous method of catalytically hydrogenating $CO_2$ using said catalyst.

DISCLOSURE OF INVENTION

The oxide-based catalyst of the present invention comprises a compound oxide having the oxide composition of CuO-ZnO-$Cr_2O_3$-$Al_2O_3$-La*$_2$O$_3$ (in which La* means La or any other lanthanide; hereinafter the same shall apply). In that case, it is preferable that the oxide composition is as follows: CuO 15 to 35% by weight, ZnO 20 to 50% by weight, $Cr_2O_3$ 0.6 to 5% by weight, $Al_2O_3$ 25 to 40% by weight and La*$_2$O$_3$ 0.5 to 8% by weight.

A method of producing the oxide-based catalyst of the present invention comprises physically admixing a compound oxide $X_1$ having the oxide composition CuO-ZnO-$Cr_2O_3$-$Al_2O_3$ with a compound oxide $X_2$ prepared by impregnating $Al_2O_3$ with a water-soluble salt of La* followed by drying and firing, to give a compound oxide having the following oxide composition: CuO 15 to 35% by weight, ZnO 20 to 50% by weight, $Cr_2O_3$ 0.6 to 5% by weight $Al_2O_3$ 25 to 40% by weight and La*$_2$O$_3$ 0.5 to 8% by weight.

Another method of producing the oxide-based catalyst of the invention comprises impregnating a compound oxide $X_1$ having the oxide composition CuO-ZnO-$Cr_2O_3$-$Al_2O_3$ with a water-soluble salt of La*, drying and firing the thus-impregnated oxide to give a compound oxide having the following oxide composition: CuO 15 to 35% by weight, ZnO 20 to 50% by weight, $Cr_2O_3$ 0.6 to 5% by weight, $Al_2O_3$ 25 to 40% by weight and La*$_2$O$_3$ 0.5 to 8% by weight.

The method of catalytically hydrogenating $CO_2$ according to the invention comprises feeding a mixed gas mainly composed of $CO_2$ and $H_2$ to a reactor and contacting said gas with an oxide-based catalyst prepared by reductively treating a compound oxide having the oxide composition CuO-ZnO-$Cr_2O_3$-$Al_2O_3$-La*$_2$O$_3$ to thereby cause conversion into a methanol-rich gas.

In the following, the invention is described in detail.
Oxide-Based Catalyst

The oxide-based catalyst of the invention comprises a compound oxide having the oxide composition CuO-ZnO-$Cr_2O_3$-$Al_2O_3$-La*$_2$O$_3$ and is reductively treated prior to use.

Usable as La* are La, Ce, Sm, etc. Considering the catalyst activity and easy availability, La and Ce are preferred.

The oxide composition is preferably as follows: CuO 15 to 35% by weight, ZnO 20 to 50% by weight, $Cr_2O_3$ 0.6 to 5% by weight, $Al_2O_3$ 25 to 40% by weight and La*$_2$O$_3$ 0.5 to 8% by weight. With such a composition, an optimal conversion of $CO_2$ and an optimal selectivity toward methanol are obtained in catalytic hydrogenation of $CO_2$.

With respect to the component La*$_2$O$_3$, for instance, when the proportion thereof is below the above range the effect of addition of La*$_2$O$_3$ is insufficient, so that the conversion of $CO_2$ and the selectivity toward methanol can be improved only slightly. Conversely, even when said proportion is increased to a level beyond the above range, the improvement in $CO_2$ conversion and methanol selectivity will be limited to a certain level while the catalyst cost becomes extremely high. This is disadvantageous from the practical viewpoint.

Production of the Oxide-Based Catalyst

The oxide-based catalyst mentioned above can be produced by the first or second method mentioned below. When comparison is made between the first and second methods, the first method can give decidedly superior results.

The first method comprises admixing a compound oxide $X_1$ having the oxide composition $CuO$-$ZnO$-$Cr_2O_3$-$Al_2O_3$ with a compound oxide $X_2$ prepared by impregnating $Al_2O_3$ with a water-soluble salt of $La^*$ and drying and firing the impregnated $Al_2O_3$. It is particularly desirable that the $Al_2O_3$ to be used in the preparation of the compound oxide $X_2$ is $\ominus$-alumina fired in advance at a temperature of 900° to 1,100° C., especially around 1,060° C. This method makes it possible to produce compound oxides having an oxide composition falling within the range mentioned above.

The second method comprises impregnating a compound oxide having the oxide composition $CuO$-$ZnO$-$Cr_2O_3$-$Al_2O_3$ with a water-soluble salt of $La^*$ and drying and firing the same. This makes it possible to obtain compound oxides having an oxide composition falling within the range mentioned above.

The water-soluble salt of $La^*$ to be used in the first and second methods includes inorganic acid salts, such as nitrate and carbonate, and various organic acid salts. The nitrate is particularly important. The hydrochloric acid salt (i.e. chloride) is not suited for the purpose of the invention, however, since negative effects presumably due to chlorine are observed.

The compound oxide $X_1$ having the oxide composition $CuO$-$ZnO$-$Cr_2O_3$-$Al_2O_3$, which is to be used in the first and second methods, is most preferably produced by contacting, in a stationary state, an aqueous solution containing a water-soluble salt each of Cu, Zn, Cr and Al with gaseous $NH_3$ to thereby cause gelation and drying and firing the gel, as detailedly reported in the Japanese Patent Application No. 02-240455 filed previously by the present inventors.

Thus, an aqueous solution is first prepared by dissolving water-soluble salts (e.g. nitrates) of Cu, Zn, Cr and Al in water. The order of addition of the salts is arbitrary. The salt concentrations should desirably be as high as possible. Then, this aqueous solution is contacted, in a stationary state, with gaseous $NH_3$ for causing gelation. In most instances, the temperature of the aqueous solution is room temperature to about 70° C. The method of contacting with gaseous $NH_3$ comprises using gaseous $NH_3$ or allowing gaseous $NH_3$ to vaporize from $NH_3$ water, for instance. In any case, the aqueous solution is preferably kept substantially unagitated while gaseous $NH_3$ is allowed to be adsorbed through the surface of the aqueous solution. The gelation is carried out generally at atmospheric pressure. It is also possible, however, to perform the gelation under pressure. After gelation, the gel is dried and then fired at a high temperature (e.g. about 300° to 500° C.), followed, as necessary, by tableting, grinding, sieving, etc.

In addition to the first and second methods, a third method is conceivable which comprises adding a water-soluble salt of $La^*$ in the step of preparing the aqueous solution by dissolving water-soluble salts (e.g. nitrates) of Cu, Zn, Cr and Al, then causing gelation, and performing drying and firing to give a compound oxide having the oxide composition $CuO$-$ZnO$-$Cr_2O_3$-$Al_2O_3$-$La^*_2O_3$. However, the compound oxides obtained by this method tend to be inferior in catalyst effect as compared with the first and second methods mentioned above.

Catalytic Hydrogenation of $CO_2$

While the oxide-based catalyst mentioned above can be used as a catalyst for various purposes, it is particularly useful as a catalyst for catalytic hydrogenation of $CO_2$. For said catalytic hydrogenation, it is necessary that the above-mentioned oxide-based catalyst be reductively treated prior to use. This reductive treatment is performed by treating with $H_2$ diluted with an inert gas such as $N_2$ at a temperature of about 200° to 500° C. for several minutes to several hours (e.g. 10 minutes to 8 hours).

The catalytic hydrogenation of $CO_2$ can be achieved by feeding a mixed gas mainly composed of $CO_2$ and $H_2$ to a reactor and contacting the mixed gas with the oxide-based catalyst mentioned above, whereby a methanol-rich gas is obtained.

The $CO_2$ component of said mixed gas may be a combustion gas discharged from a thermoelectric power station or an iron mill, or a $CO_2$ fraction separated from combustion gas, natural gas, petroleum refinery gas, byproduct gas in ammonia synthesis, coke oven gas or the like by such means as the membrane separation method, pressure swing method or absorption separation method. The $H_2$ component may be $H_2$ obtained by electrolysis of water, $H_2$ supplied from some other process in the same plant or from some other plant, for instance.

The mixing ratio between $CO_2$ and $H_2$, when expressed in terms of mole ratio, is theoretically 1:3 but may be within the range of about 2:8 to 7:3. In case it contains CO, the mixed gas may be fed as the raw material gas after suitably adjusting the proportion of $CO_2$.

Within limits harmless to the purpose of the invention, the raw material gas may contain one or more components other than $CO_2$ and $H_2$, for example $N_2$, CO, $H_2O$, hydrocarbons, alcohols, etc. It is necessary, however, that sulfur-containing compounds and nitrogen oxides, which may possibly act as catalyst poisons, and $O_2$, which may possibly retard the rate of reaction, should be removed beforehand to levels below the respective tolerance limits.

The reactor is packed with the above oxide-based catalyst in the form of a fixed bed or fluidizable bed. The reductive treatment of the oxide-based catalyst may be performed after packing the reactor with the compound oxide $CuO$-$ZnO$-$Cr_2O_3$-$Al_2O_3$-$La^*_2O_3$. This reactor is constructed so that it can be heated.

The reaction pressure is suitably about 20 to 120 atmospheres, preferably about 30 to 100 atmospheres, and the reaction temperature is suitably about 150° to 300° C., preferably about 200° to 280° C. When the pressure is too low, the $CO_2$ conversion rate and methanol selectivity decrease while excessively high pressures are disadvantageous from the viewpoints of equipment cost and energy cost. When the temperature is too low, the $CO_2$ conversion rate and methanol selectivity will decrease and, when the temperature is excessively high, the methanation reaction progresses preferentially and, in addition, the process is disadvantageous from the energy viewpoint.

The effluent from the reactor may be partly recycled to the inlet side of the reactor.

The product methanol obtained by the above reaction can be used for various purposes. It is preferable, however, to produce liquid hydrocarbons using this methanol as a starting material. In this case, an H-form Fe silicate catalyst is optimal as the catalyst. For the production of liquid hydrocarbons, it is possible to obtain liquid hydrocarbons from $CO_2$ and $H_2$ at a stroke by using the reactor mentioned previously as a first reactor and a reactor packed with an H-form Fe silicate as a second reactor and connecting both the reactors in series. A method of producing the H-form Fe silicate and reaction conditions in the second reactor are detailedly described in the Japanese Patent Application No. 02-240454 filed by the present inventors.

Working

When the compound oxide of the invention having the oxide composition $CuO\text{-}ZnO\text{-}Cr_2O_3\text{-}Al_2O_3\text{-}La^*_2O_3$ is reductively treated and then used as a catalyst for catalytic hydrogenation of $CO_2$, incomparably good effects are produced as compared with the catalysts proposed so far. Even when compared with the catalyst obtained by reductive treatment of a compound oxide $X_1$ having the oxide composition $CuO\text{-}ZnO\text{-}Cr_2O_3\text{-}Al_2O_3$ as already proposed by the present inventors, markedly improved $CO_2$ conversion and methanol selectivity can be obtained.

As regards the mechanisms, it is presumable that since the $La^*_2O_3$ appropriately distributed on the catalyst surface has weak basicity, the $La^*_2O_3$ facilitates the adsorption of $CO_2$ contained in the raw material gas on the catalyst without inhibiting active sites on the catalyst.

Effects of the Invention

When the oxide-based catalyst of the invention is used, the conversion of $CO_2$ and the selectivity toward methanol in the catalytic hydogenation reaction of $CO_2$ are markedly improved as compared with the prior art catalysts, attaining the level of commercial practicability.

BEST MODES FOR CARRYING OUT THE INVENTION

Figure 1:
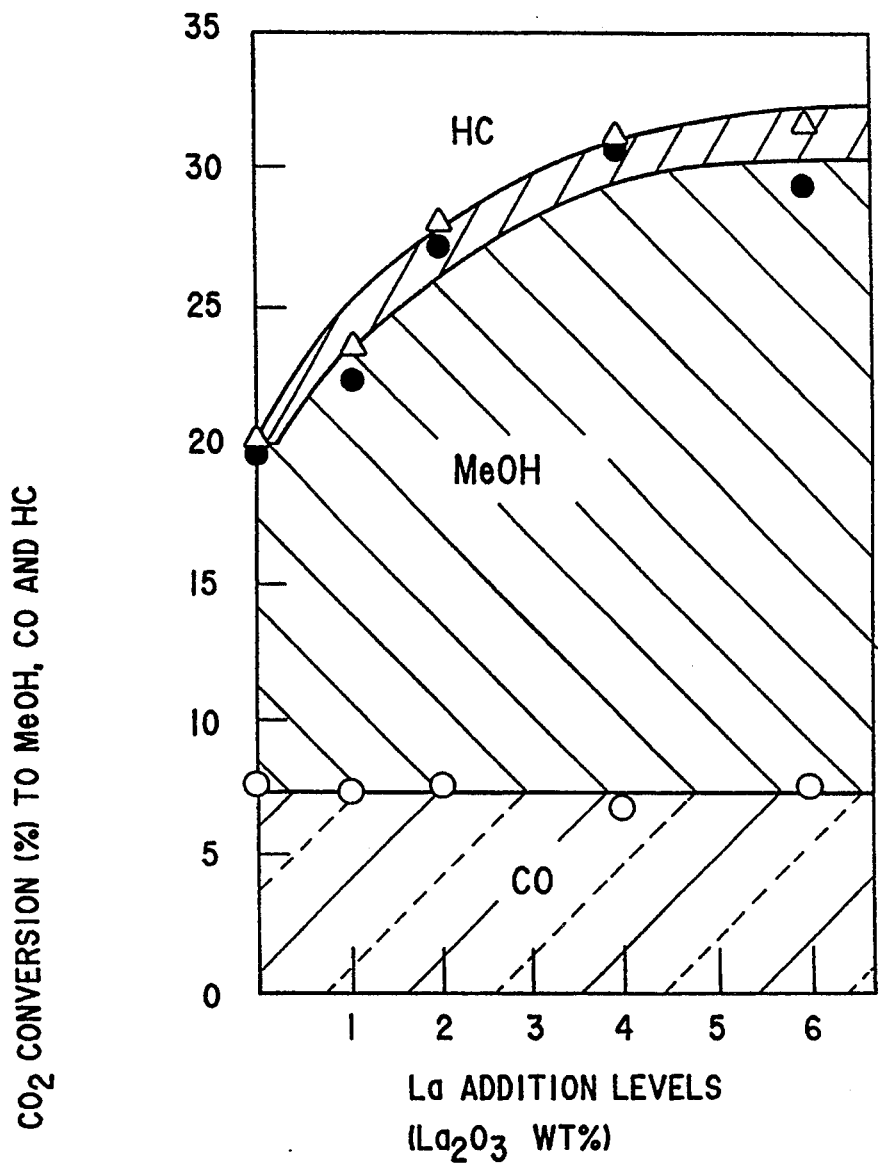
FIG. 1 is a graphic representation of the influence of the level of addition of La on the catalytic hydrogenation reaction of $CO_2$.

The following examples further illustrate the present invention.

EXAMPLE 1

Preparation of an Oxide-Based Catalyst
First Method

A high-concentration aqueous solution was prepared according to the following formulation.

| | |
|---|---|
| $Cu(NO_3)_2 \cdot 3H_2O$ | 3.82 g |
| $Zn(NO_3)_2 \cdot 6H_2O$ | 7.57 g |
| $Cr(NO_3)_3 \cdot 9H_2O$ | 0.29 g |
| $Al(NO_3)_3 \cdot 9H_2O$ | 7.86 g |
| Water | 65.0 g |

This aqueous solution (84.5 g) was placed in a tray and allowed to stand in a constant-temperature vessel maintained at 60° C. and, further, another tray containing 150 ml of aqueous ammonia with a concentration of 28% by weight was placed in this constant-temperature vessel and allowed to stand for 15 minutes. The aqueous solution absorbed the gaseous ammonia that had evaporated, whereby said solution gelated.

The gel thus obtained was dried overnight at a temperature of 120° C., then the temperature was raised from room temperature to 150° C. over 30 minutes under an atmosphere of air and then from 150° C. to 350° C. over 2 hours, and the gel was further fired at 350° C. for 3 hours.

The fired product was allowed to cool, molded by tabulating, then ground and sieved and a 10–24 mesh fraction was collected. A $CuO\text{-}ZnO\text{-}Cr_2O_3\text{-}Al_2O_3$-based compound oxide was thus obtained. This is referred to as $X_1$.

Separately, an aqueous solution was prepared by dissolving 0.55 g of $La(NO_3)_3 \cdot 6H_2O$ in 1.0 g of water, and 0.54 g of $\ominus$-alumina fired beforehand at 1,060° C. was impregnated with the aqueous solution, then dried and further fired at 350° C. for 3 hours. The thus-obtained compound oxide is referred to as $X_2$.

This compound oxide $X_2$ was admixed with the above-mentioned compound oxide $X_1$ in a mortar for physical blending, whereby a $CuO\text{-}ZnO\text{-}Cr_2O_3\text{-}Al_2O_3\text{-}La_2O_3$-based compound oxide having the following oxide composition was obtained:

| | |
|---|---|
| CuO | 24.2% by weight |
| ZnO | 39.8% by weight |
| $Cr_2O_3$ | 1.1% by weight |
| $Al_2O_3$ | 30.9% by weight |
| $La_2O_3$ | 4.0% by weight |

Hereinafter, this method is referred to as "first method".

Catalytic Hydrogenation Reaction

A reactor made of a stainless steel pipe having an inside diameter of 10 mm as placed in an oven was packed with 1.8 ml of the $CuO\text{-}ZnO\text{-}Cr_2O_3\text{-}Al_2O_3\text{-}La_2O_3$ compound oxide obtained as described above, and the catalyst was reductively treated by passing an $H_2$ gas stream diluted with $N_2$ to a concentration of 1% by volume at a flow rate of 100 ml per minute while raising the temperature from room temperature to 500° C. over 1 hour and then further maintaining the temperature at 500° C. for 30 minutes.

Then, a mixed gas composed of 25% by volume of $CO_2$ and 75% by volume of $H_2$ was fed from a cylinder filled with this mixed gas to the above reactor and the reaction was carried out under the following conditions: pressure 50 atmospheres, temperature 250° C. and space velocity 4,700 $hr^{-1}$.

The effluent gas from the reactor was sampled and analyzed on a gas chromatograph equipped with an integrator, whereby the following results were obtained:

| | |
|---|---|
| Total $CO_2$ conversion | 31.0% |
| Conversion to methanol | 22.9% (selectivity toward methanol 73.9%) |
| Conversion to CO | 7.1% (selectivity toward CO 22.9%) |
| Conversion to other components | 1.0% (selectivity toward other components 3.2%) |

The other components were mostly hydrocarbons. These results are unbelievably good from the viewpoint of prior art common sense.

Second Method

For reference, a $CuO$-$ZnO$-$Cr_2O_3$-$Al_2O_3$-based compound oxide was prepared by causing gelation, drying and firing in the same manner as in Example 1 except that the amount of $Al(NO_3)_3 \cdot 9H_2O$ was increased to 11.83 g. This compound oxide was impregnated with an aqueous solution prepared by dissolving 0.55 g of $La(NO_3)_3 \cdot 6H_2O$ in 1.0 g of water and then fired again at the same temperature of 350° C. for 3 hours, whereby a $CuO$-$ZnO$-$Cr_2O_3$-$Al_2O_3$-$La_2O_3$-based compound oxide having the same oxide composition as that obtained by the first method was obtained. Hereinafter, this method is referred to as "second method".

This compound oxide was reduced and, using the thus-obtained catalyst, the reaction procedure of Example 1 was repeated under the same conditions as employed for the first method catalyst. The effluent gas from the reactor was sampled and analyzed to give the following results:

| Total $CO_2$ conversion | 24.4% |
|---|---|
| Conversion to methanol | 14.1% (selectivity toward methanol 57.8%) |
| Conversion to CO | 9.0% (selectivity towered CO 36.9%) |
| Conversion to other components | 1.3% (selectivity toward other components 5.3%) |

The fact that the second method is inferior to the first method is presumably due to the difference in the degree of dispersion as resulting from the difference in surface area.

Third Method

For further reference, a high-concentration aqueous solution was prepared according to the formulation:

| $Cu(NO_3)_2 \cdot 3H_2O$ | 3.82 g |
|---|---|
| $Zn(NO_3)_2 \cdot 6H_2O$ | 7.57 g |
| $Cr(NO_3)_2 \cdot 9H_2O$ | 0.29 g |
| $Al(NO_3)_2 \cdot 9H_2O$ | 11.83 g |
| $La(NO_2)_3 \cdot 6H_2O$ | 0.55 g |
| Water | 65.0 g | and a $CuO$-$ZnO$-$Cr_2O_3$-$Al_2O_3$-$La_2O_3$-based compound oxide having the same oxide composition as in the first method was prepared by causing gelation, drying and firing in the same manner as in the first method. Hereinafter, this method is referred to as "third method".

This compound oxide was reduced and, using the thus-obtained catalyst, the reaction procedure of Example 1 was repeated under the same reaction conditions as employed for the first method catalyst. The effluent gas from the reactor was sampled and analyzed to give the following results;

| Total $CO_2$ conversion | 11.1% |
|---|---|
| Conversion to methanol | 7.0% (selectivity toward methanol 63.1%) |
| Conversion to CO | 4.1% (selectivity toward CO 36.9%) |
| Conversion to other components | trace (selectivity toward other components trace) |

It is evident that these results are inferior not only to those of the first and second methods but also to the results obtained without adding La as mentioned below in Comparative Example 1.

COMPARATIVE EXAMPLE 1

3.82 g of $Cu(NO_3)_2 \cdot 3H_2O$, 7.57 g of $Zn(NO_3)_2 \cdot 6H_2O$, 0.29 g of $Cr(NO_3)_3 \cdot 9H_2O$, 11.83 g of $Al(NO_3)_3 \cdot 9H_2O$ and 50.0 g of water were respectively weighted. The salts were dissolved in water to give 73.5 g of a high-concentration aqueous solution. The percentage proportions of the respective components were as follows:

| $Cu(NO_3)_2 \cdot 3H_2O$ | 5.2% by weight |
|---|---|
| $Zn(NO_3)_2 \cdot 6H_2O$ | 10.3% by weight |
| $Cr(NO_3)_3 \cdot 9H_2O$ | 0.4% by weight |
| $Al(NO_3)_3 \cdot 9H_2O$ | 16.1% by weight |
| Water | 68.0% by weight |

Using this aqueous solution (73.5 g), gelation, firing, molding by tableting, grinding and sieving were carried out under the same conditions as mentioned in Example 1 for the production of $X_1$ by the first method, whereby a $CuO$-$ZnO$-$Cr_2O_3$-$Al_2O_3$-based compound oxide having the following oxide composition was obtained.

| CuO | 25.2% by weight |
|---|---|
| ZnO | 41.5% by weight |
| $Cr_2O_3$ | 1.1% by weight |
| $Al_2O_3$ | 32.2% by weight |

This compound oxide was reductively treated under the same conditions as used for the first method in Example 1.

The reaction was carried out using this catalyst under otherwise the same conditions as used in Example 1 for the first method catalyst. The effluent gas from the reactor was sampled and analyzed to give the following results:

| Total $CO_2$ conversion | 20.8% |
|---|---|
| Conversion to methanol | 12.0% (selectivity toward methanol 57.7%) |
| Conversion to CO | 8.4% (selectivity toward CO 40.4%) |
| Conversion to other components | 0.4% (selectivity toward other components 1.9%) |

EXAMPLE 2

To investigate the influence of the level of addition of La, a $CuO$-$ZnO$-$Cr_2O_3$-$Al_2O_3$-based compound oxide having the oxide composition:

| CuO | 25.0% by weight |
|---|---|
| ZnO | 41.5% by weight |
| $Cr_2O_3$ | 1.2% by weight |
| $Al_2O_3$ | 32.3% by weight | was used as a reference and compound oxides were produced by the first method mentioned in Example 1 while adding to said reference 1% by weight, 2% by weight, 3% by weight, 4% by weight or 6% by weight of $La_2O_3$. The compound oxides obtained were examined for their reactivity under the same conditions as used for the first method catalyst of Example 1.

FIG. 1 shows the results, which were obtained under the following conditions:

SV=4,700 hr$^{-1}$ (on the catalyst basis),
250° C., 50 atmospheres,
$H_2:CO_2$=75:25 (vol. %).

From FIG. 1, it is seen that the conversion of $CO_2$ and the selectivity toward methanol tend to increase with the increase of the La addition level and become nearly constant at La addition levels not lower than 4% by weight (as $La_2O_3$).

COMPARATIVE EXAMPLE 2

Following the procedure of the first method as used for producing the compound oxide $X_2$ in Example 1, La was caused to be supported on $\ominus$-$Al_2O_3$ in an amount of 4% by weight as $La_2O_3$ and the reactivity was examined under the same conditions as used in Example 1 for the first method catalyst. In this case, however, the formation of methanol or CO was hardly observed. Only slight amounts of hydrocarbons were formed.

EXAMPLE 3

To investigate the influences of the reaction conditions, the reaction was carried out using the same CuO-ZnO-$Cr_2O_3$-$Al_2O_3$-$La_2O_3$-based compound oxide ($La_2O_3$: 4% by weight) as that prepared in Example 1 by the first method, as follows:

(a) The temperature was varied within the range of 220° to 290° C., while the other conditions were the same as used in Example 1 for the first method catalyst, namely the pressure was 50 atmospheres and the space velocity was 4,700 hr$^{-1}$.

(b) The reaction pressure was varied within the range of 20 to 80 atmospheres, while the other conditions were the same as used in Example 1 for the first method catalyst, namely the temperature was 250° C. and the space velocity was 4,700 hr$^{-1}$.

Figure 2:
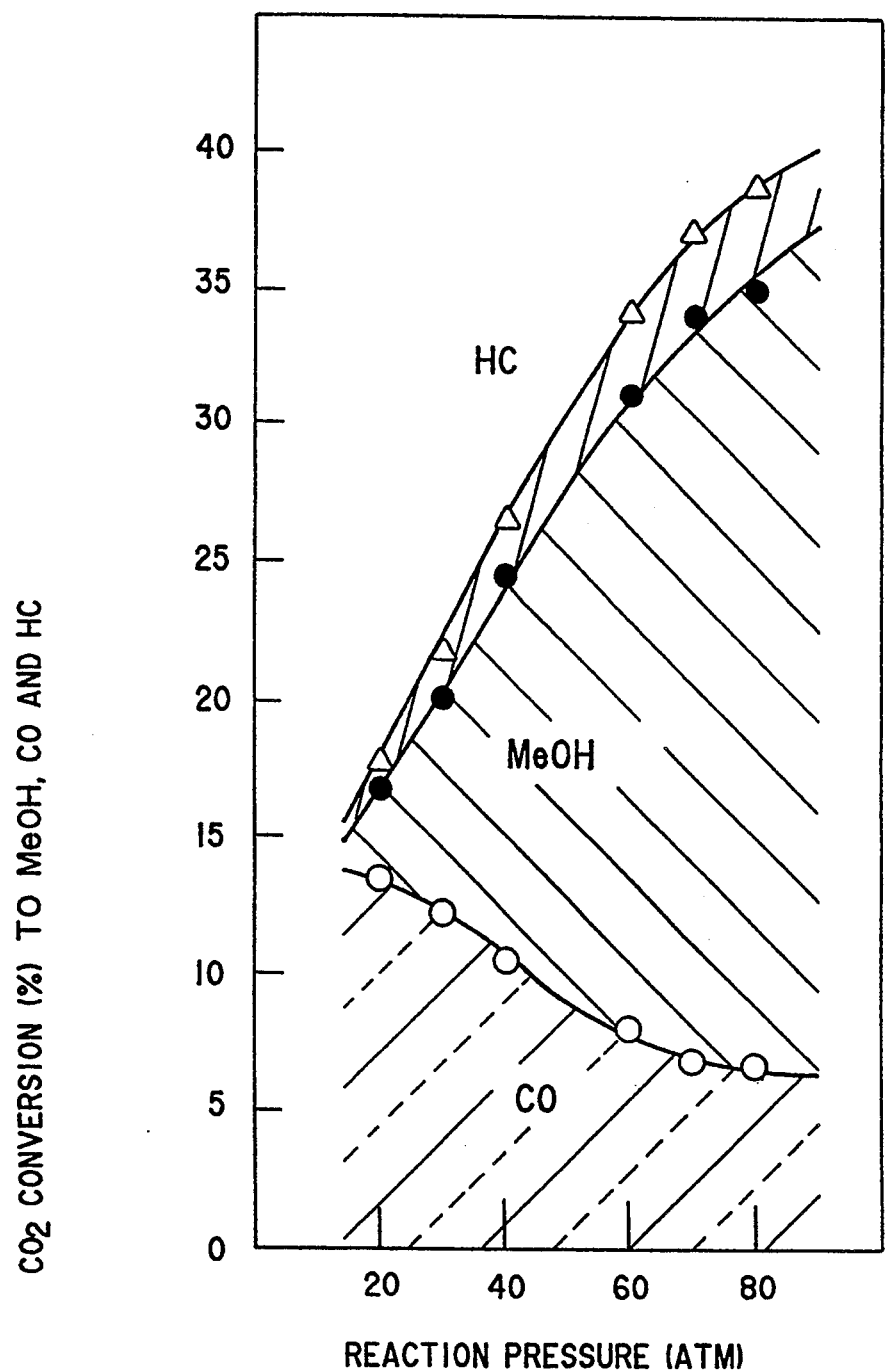
FIG. 2 is a graphic representation of the influence of the reaction pressure on the catalytic hydrogenation reaction of $CO_2$.

The results of the experiment (a) revealed that the temperature of 250° C. is optimal for the reaction. Therefore, the experiment (b) was performed at the fixed temperature of 250° C. The results of the experiment (b) are shown in FIG. 2. For FIG. 2, the conditions were as follows:

Catalyst with La added in an amount of 4% by weight as $La_2O_3$
SV=4,700 hr$^{-1}$ (based on the compound oxide catalyst $X_1$);
250° C., 20 to 80 atmospheres.

From FIG. 2, it is seen that the conversion of $CO_2$ and the selectivity toward methanol increase markedly as the reaction pressure increases. For example, high performance characteristics are obtained at the pressure of 80 atmospheres, the total conversion of $CO_2$ amounts to 39% and the conversion to methanol to 29% (selectivity toward methanol 74%). From FIG. 2, it is also evident that a successive reaction process is observable; thus, CO is mainly formed on the low-pressure side while, on the high-pressure side, the selectivity toward methanol increases.

INDUSTRIAL APPLICABILITY

The oxide-based catalyst of the invention is useful particularly as a catalyst for converting a $CO_2$-containing gas into methanol or some other useful fraction such as a liquid fuel.

I claim:

1. An oxide-based catalyst which comprises a compound oxide having the oxide composition CuO-ZnO-$Cr_2O_3$-$Al_2O_3$-$La^*_2O_3$ ($La^*$ being La or any other lanthanide), wherein the oxide composition is as follows: CuO 15 to 35% by weight, ZnO 20 to 50% by weight, $Cr_2O_3$ 0.6 to 5% by weight, $Al_2O_3$ 25 to 40% by weight and $La^*_2O_3$ 0.5 to 8% by weight, based on the total weight of the composition.

2. A method of producing an oxide-based catalyst which comprises physically admixing a compound oxide $X_1$ having the oxide composition CuO-ZnO-$Cr_2O_3$-$Al_2O_3$ with a compound oxide $X_2$ prepared by impregnating $Al_2O_3$ with a water-soluble salt of $La^*$ ($La^*$ being La or any other lanthanide) and drying and firing the impregnated $Al_2O_3$ to give a compound oxide having the following oxide composition: CuO 15 to 35% by weight, ZnO 20 to 50% by weight, $Cr_2O_3$ 0.6 to 5% by weight, $Al_2O_3$ 25 to 40% by weight and $La^*_2O_3$ 0.5 to 8% by weight., based on the total weight of the composition.

3. The method of claim 2 wherein the $Al_2O_3$ to be used in preparing the compound oxide $X_2$ is $\ominus$-alumina fired at 900° to 1,100° C. prior to impregnation with $La^*$.

4. A method of producing an oxide-based catalyst which comprises impregnating a compound oxide $X_1$ having the oxide composition CuO-ZnO-$Cr_2O_3$-$Al_2O_3$ with a water-soluble salt of $La^*$ ($La^*$ being La or any other lanthanide) and drying and firing the impregnated compound oxide to give a compound oxide having the following oxide composition: CuO 15 to 35% by weight, ZnO 20 to 50% by weight, $Cr_2O_3$ 0.6 to 5% by weight, $Al_2O_3$ 25 to 40% by weight and $La^*_2O_3$ 0.5 to 8% by weight, based on the total weight of the composition.

5. A method of catalytically hydrogenating $CO_2$ which comprises feeding a mixed gas mainly composed of $CO_2$ and $H_2$ to a reactor and contacting said gas with an oxide-based catalyst prepared by reductively treating a compound oxide having the oxide composition CuO-ZnO-$Cr_2O_3$-$Al_2O_3$-$La^*_2O_3$ ($La^*$ being La or any other lanthanide) to thereby cause conversion into a methanol-rich gas, under a reaction pressure of from 20 to 120 atmospheres at a reaction temperature of from 150° to 300° C. wherein the oxide composition is as follows: CuO 15 to 35% by weight, ZnO 20 to 50% by weight, $Cr_2O_3$ 0.6 to 5% by weight, $Al_2O_3$ 25 to 40% by weight and $La^*_2O_3$ 0.5 to 8% by weight, based on the total weight of the composition.

6. An oxide-based catalyst for catalytic hydrogenation of $CO_2$ which comprises a compound oxide having the oxide composition CuO-ZnO-$Cr_2O_3$-$Al_2O_3$-$La^*_2O_3$ ($La^*$ being La or any other lanthanide), wherein the oxide composition is as follows: CuO 15 to 35% by weight, ZnO 20 to 50% by weight, $Cr_2O_3$ 0.6 to 5% by weight, $Al_2O_3$ 25 to 40% by weight and $La^*_2O_3$ 0.5 to 8% by weight, based on the total weight of the composition.

7. A method of producing an oxide-based catalyst for catalytic hydrogenation of $CO_2$ which comprises physically admixing a compound oxide $X_1$ having the oxide composition $CuO$-$ZnO$-$Cr_2O_3$-$Al_2O_3$ with a compound oxide $X_2$ prepared by impregnating $Al_2O_3$ with a water-soluble salt of La* (La* being La or any other lanthanide) and drying and firing the impregnated $Al_2O_3$ to give a compound oxide having the following oxide composition: $CuO$ 15 to 35% by weight, $ZnO$ 20 to 50% by weight, $Cr_2O_3$ 0.6 to 5% by weight, $Al_2O_3$ 25 to 40% by weight and $La*_2O_3$ 0.5 to 8% by weight, based on the total weight of the composition.

8. The method of claim 7, wherein the $Al_2O_3$ to be used in preparing the compound oxide $X_2$ is γ-alumina fired at 900° to 1,100° C. prior to impregnation with La*.

9. A method of producing an oxide-based catalyst for catalytic hydrogenation of $CO_2$ which comprises impregnating a compound oxide $X_1$ having the oxide composition $CuO$-$ZnO$-$Cr_2O_3$-$Al_2O_3$ with a water-soluble salt of La* (La* being La or any other lanthanide) and drying and firing the impregnated compound oxide to give a compound oxide having the following oxide composition: $CuO$ 15 to 35% by weight, $ZnO$ 20 to 50% by weight, $Cr_2O_3$ 0.6 to 5% by weight, $Al_2O_3$ 25 to 40% by weight and $La*_2O_3$ 0.5 to 8% by weight, based on the total weight of the composition.

* * * * *